(12) United States Patent
Ishiguro et al.

(10) Patent No.: US 6,170,487 B1
(45) Date of Patent: Jan. 9, 2001

(54) HEALTH SUPPORT DEVICE AND METHOD OF PRODUCING THE SAME

(75) Inventors: Saburo Ishiguro, Tokyo; Yoshitsugu Fujita, Koganei; Tetsuhiro Iwata, Iwaki, all of (JP)

(73) Assignee: Furukawa Co., Ltd., Tokyo (JP)

( * ) Notice: Under 35 U.S.C. 154(b), the term of this patent shall be extended for 0 days.

(21) Appl. No.: 09/175,402

(22) Filed: Oct. 20, 1998

(30) Foreign Application Priority Data

Apr. 1, 1998 (JP) .................................................. 10-088738

(51) Int. Cl.$^7$ .................................................... A61B 19/00
(52) U.S. Cl. ................................................................ 128/897
(58) Field of Search .............................. 128/897; 607/1; 136/251

(56) References Cited

U.S. PATENT DOCUMENTS

| | | | |
|---|---|---|---|
| 5,389,159 | * 2/1995 | Kataoka et al. | 136/251 |
| 5,607,453 | 3/1997 | Ishiguro et al. | |
| 5,814,078 | * 9/1998 | Zhou et al. | 607/1 |

* cited by examiner

*Primary Examiner*—Max Hindenburg
*Assistant Examiner*—Brian Szmal
(74) *Attorney, Agent, or Firm*—Armstrong, Westerman, Hattori, McLeland & Naughton

(57) ABSTRACT

A health support device having a lamination of a semiconductor film on a surface of a partially-reduced sintered material of titanium oxide. The semiconductor film is preferably a p-type semiconductor film of silicon or germanium. The partially-reduced sintered material is preferably represented by $TiO_{2-x}$, where $0<x<0.5$. The thickness of the semiconductor film is preferably from 1 nm to 500 nm. In production, a mixture of a titanium oxide powder and a binder is press-molded, and the molded material is sintered at a temperature of from 500° C. to 1100° C. in a vacuum, inert or reducing atmosphere. A p-type semiconductor film is formed on a surface of the resulting partially-reduced sintered material of titanium oxide.

6 Claims, 1 Drawing Sheet

HEALTH SUPPORT DEVICE AND METHOD OF PRODUCING THE SAME

BACKGROUND OF THE INVENTION

The present invention relates to a health support device. More particularly, the present invention relates to an improved health support device using titanium oxide as a base material.

The present inventors previously developed a composite medical treating device in which laminations of an n-type semiconductor film and a p-type semiconductor film are coated on a surface of a ferrodielectric substance as a base material (see Japanese Patent Laid-Open Publication Hei 8-10339). However, the production of the composite medical treating device requires a large number of processing steps and therefore takes much time and labor, resulting in high cost.

The present inventors further conducted studies and have found that a health support device that exhibits even more excellent medical treating effect is obtained by employing a partially-reduced sintered material of titanium oxide as a base material.

SUMMARY OF THE INVENTION

The present invention solves the problems in the above-described prior art, and it is an object of the present invention to provide a health support device that is effective in curing disorders of a wide variety of organs. It is another object of the present invention to provide a method of producing the health support device.

The present invention provides a health support device including a partially-reduced sintered material of titanium oxide, and a lamination of a semiconductor film formed on a surface of the partially-reduced sintered material.

In addition, the present invention provides a health support device including a partially-reduced sintered material of titanium oxide, and a lamination of a p-type semiconductor film formed on a surface of the partially-reduced sintered material.

In either of the above-described health support devices, the semiconductor film may be of silicon or germanium.

In any one of the above-described health support devices, the partially-reduced sintered material of titanium oxide may be a low-order oxide of titanium represented by $TiO_{2-x}$, where $0<x<0.5$.

In any one of the above-described health support devices, the semiconductor film may have a thickness of from 1 nanometer to 500 nanometers.

In addition, the present invention provides a method of producing a health support device. The method includes the steps of: pressure-molding a mixture of a titanium oxide powder and a binder to form a molded material; sintering the molded material at a temperature of from 500° C. to 1100° C. in a vacuum atmosphere, an inert atmosphere or a reducing atmosphere to obtain a partially-reduced sintered material of titanium oxide; and forming a p-type semiconductor film on a surface of the partially-reduced sintered material of titanium oxide.

In addition, the present invention provides a method of producing a health support device. The method includes the steps of: pressure-molding a mixture of a titanium oxide powder and a binder that exhibits a reducing action during sintering to form a molded material; sintering the molded material to obtain a partially-reduced sintered material of titanium oxide; and forming a p-type semiconductor film on a surface of the partially-reduced sintered material of titanium oxide.

In either of the above-described methods, the binder may be at least one selected from the group consisting of varnishes, starches, and polyvinyl alcohol.

In any one of the above-described methods, the partially-reduced sintered material of titanium oxide may be a low-order oxide of titanium represented by $TiO_{2-x}$, where $0<x<0.5$.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

DESCRIPTION OF THE PREFERRED EMBODIMENTS

Figure 1A:
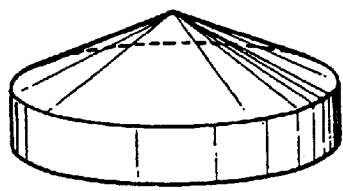
FIGS. 1(a)–1(e) show various shapes usable for the health support device according to the present invention.

The present invention will be described below in detail with reference to the accompanying drawing.

Titanium oxide is generally a white solid represented by the molecular formula of $TiO_2$ and having a forbidden band width (band gap) of 3.0 eV. If such titanium oxide is heated at a temperature of from 500° C. to 1100° C. in a vacuum or in a stream of hydrogen, oxygen in the titanium oxide is partially lost, and the color changes to gray or black. As a result, a low-order oxide of titanium represented by $TiO_{2-x}$, is obtained. Such a low-order oxide of titanium is also obtained by heating a molded mixture of titanium oxide and a small amount of a carbon compound (e.g. a binder such as a varnish, starch, or a polyvinyl alcohol) at a temperature of from 500° C. to 1100° C. in a vacuum or an inert atmosphere.

This is surmised as follows. The heating process brings about a change in the electronic structure of titanium oxide and causes a defect level of oxygen. Consequently, absorption of visible light rays occurs, and thus the partially-reduced titanium oxide appears black.

In general, titanium oxide is a substance having a high radiation efficiency for far infrared rays, and it is considered according to the theory of black body radiation that black partially-reduced titanium oxide exhibits an even higher far infrared radiation efficiency.

For example, production of partially-reduced titanium oxide used in the present invention may be carried out by heating powdered titanium oxide ($TiO_2$: rutile type or anatase type) at a temperature of from 500° C. to 1100° C., preferably from 600° C. to 900° C., in a vacuum or an inert or reducing atmosphere.

Examples of inert atmospheres usable in the present invention are a nitrogen gas atmosphere and an argon gas atmosphere. Examples of reducing atmospheres usable in the present invention are a hydrogen gas atmosphere and a carbon monoxide gas atmosphere.

The partially-reduced sintered material of titanium oxide according to the present invention can also be obtained by pressure-molding the partially-reduced sintered material powder obtained as described above. After the pressure molding, the molded material may be re-sintered on heating. A partially-reduced sintered material can also be obtained by pressure-molding a mixture of a titanium oxide powder and a binder and heating the resulting molded material in the above-described atmosphere. Examples of binders usable in the present invention are varnishes, starches, and polyvinyl alcohol.

Depending on the heating temperature and heating time for titanium oxide, x in the resulting partially-reduced titanium oxide, which is represented by $TiO_{2-x}$, varies within the range of $0<x<0.5$.

The color tone of the titanium oxide also varies within the range of from white through gray to black.

It should be noted that the degree of vacuum in the above-described vacuum atmosphere is preferably within the range of from $10^{-2}$ to $10^{-6}$ mmHg.

Generally, titanium oxide ($TiO_2$) is a compound having a forbidden band width of 3.0 eV. As the titanium oxide is partially reduced, the combined oxygen gradually separates, causing a defect level of oxygen. Consequently, the partially-reduced titanium oxide absorbs light and thus appears black. Titanium oxide exhibits a high far infrared radiation efficiency, and when it is partially reduced, the wavelength region of far infrared radiation widens. Meanwhile, it is considered that the wavelength region of radiation that acts effectively on the disorder of each particular organ of the body varies according to the kind of organ. Therefore, it is surmised that partially-reduced $TiO_{2-x}$ ($0<x<0.5$) can cope with a wide wavelength region and exhibit a high degree of effectiveness in comparison to simple $TiO_2$.

However, if titanium oxide ($TiO_2$) is further reduced to $Ti_2O_3$, the structure changes, and the forbidden band width becomes constant. Consequently, the effectiveness in curing physical disorders lowers unfavorably.

Therefore, according to the present invention, partially-reduced titanium oxide represented by $TiO_{2-x}$ ($0<x<0.5$) is coated with a semiconductor film, e.g. a p-type silicon semiconductor thin film or a p-type germanium semiconductor thin film, thereby providing a health support device that is effective in curing disorders of a wide variety of organs.

Formation of a semiconductor film, e.g. a p-type silicon semiconductor film or a p-type germanium semiconductor film, on a surface of the partially-reduced titanium oxide sintered material may be carried out by sputtering, CVD, MOCVD, coating, etc. The thickness of the semiconductor film is preferably within the range of from 1 nm to 500 nm, particularly preferably from 50 nm to 200 nm.

A film thickness of less than 1 nm is not sufficiently effective in curing the affected part of an organ by wave radiation. If the film thickness exceeds 500 nm, the health support device provides only the curing effect by wave radiation by the semiconductor, and it becomes difficult for the partially-reduced titanium oxide inside the device to manifest the far infrared radiation effect over a wide wavelength region to the outside.

Figure 1B:
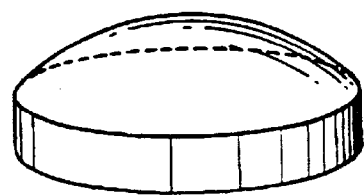
Figure 1C:
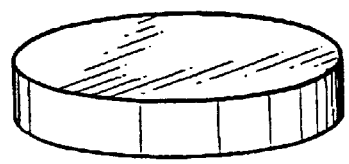
Figure 1D:
Figure 1E:
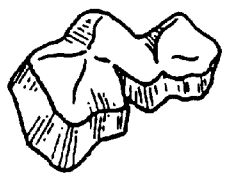

Regarding the shape of the product, it is possible to use various shapes as shown in FIG. 1. That is, the health support device may have a conical columnar shape (in which the upper part is conical and the lower part is a short circular column) as shown in part (a) of the figure, or a spherical columnar shape (in which the upper part is hemispherical and the lower part is a short circular column) as shown in part (b) of the figure. It is also possible to use a disk shape, a spherical shape, and an irregular mass shape as shown in parts (c), (d) and (e) of the figure.

EXAMPLE 1

To a commercially available titanium oxide ($TiO_2$) powder (rutile type having an average particle diameter of 0.6 μm; manufactured by Furukawa Co., Ltd.), 2% of silicone varnish as a binder was added and mixed thoroughly. Thereafter, the mixture was press-molded in a mold under a pressure of about 1,000 kgf/cm² to obtain a molded material with a conical columnar shape (in which the upper part was conical and the lower part was a short circular column) as shown in part (a) of FIG. 1 (which is a perspective view showing the external appearance) having a diameter of 6 mm and a height of 3 mm (column height: 2 mm).

The molded material was sintered by heating at 1000° C. for 2 hours in a vacuum to obtain a black partially-reduced titanium oxide ($TiO_{1.91}$) sintered material.

A p-type silicon semiconductor film (thickness: 100 nm) was coated on the black partially-reduced titanium oxide sintered material. For the product thus obtained, feeble magnetic wave radiation with respect to various organs and so forth was measured. Results of the measurement are shown in Table 1 below.

It should be noted that feeble magnetic wave radiation was measured by using "MIRS" (trade name: a magnetic wave resonance analyzer manufactured by Acty Two-One K.K.). The measuring apparatus (MIRS) indicates a numerical value of feeble magnetic wave radiation in the range of from +21 to −21. With respect to various organs, the best value is +21, and the worst value is −21. Such a feeble magnetic wave resonance analyzer is publicly known, being disclosed, for example, in U.S. Pat. Nos. 5,317,265, 5,517,119 and 5,607,453.

TABLE 1

|  | Example 1 | Comparative Example 1 | Comparative Example 2 |
| --- | --- | --- | --- |
| Titanium oxide base p-type silicon thin film | $TiO_{1.91}$ present | $TiO_2$ present | $Ti_2O_3$ present |
| Immunity | +21 | +18 | +17 |
| Stomach | +19 | +13 | +15 |
| Large intestine | +19 | +16 | — |
| Liver | +20 | +17 | +13 |
| Kidney | +19 | +18 | — |
| Pancreas | +17 | +15 | — |
| Heart | +19 | +15 | — |
| Blood circulation | +21 | +16 | +16 |
| Autonomous nervous system | +20 | +20 | +15 |
| Prostate gland | +19 | +16 | — |
| Pain | +21 | +17 | +14 |
| Eyestrain | +21 | +19 | — |

[Range of feeble magnetic wave radiation numerical values: from +21 (best value) to −21 (worst value)]
[Equipment used: MIRS]

COMPARATIVE EXAMPLE 1

To a commercially available titanium oxide ($TiO_2$) powder (rutile type having an average particle diameter of 0.6 μm; manufactured by Furukawa Co., Ltd.), 2% of silicone varnish as a binder was added and mixed thoroughly. Thereafter, the mixture was press-molded in a mold under a pressure of about 1,000 kgf/cm² to obtain a molded material with a conical columnar shape as shown in part (a) of FIG. 1, which was the same as in Example 1.

The molded material was sintered by heating at 1000° C. for 2 hours in the air. Consequently, a white titanium oxide ($TiO_2$) sintered material was obtained.

A p-type silicon semiconductor film (thickness: 100 nm) doped with boron at 200 at ppm was coated on the white titanium oxide sintered material. For the product thus obtained, feeble magnetic wave radiation with respect to various organs and so forth was measured. Results of the measurement are shown in Table 1.

COMPARATIVE EXAMPLE 2

To a finely divided titanium oxide ($Ti_2O_3$) powder, 2% of silicone varnish as a binder was added and mixed thoroughly. Thereafter, the mixture was press-molded in a mold under a pressure of about 1,000 kgf/cm$^2$ to obtain a molded material with a conical columnar shape as shown in part (a) of FIG. 1, which was the same as in Example 1.

The molded material was sintered by heating at 1000° C. for 2 hours in a nitrogen atmosphere. Consequently, a gray titanium oxide ($Ti_2O_3$) sintered material was obtained.

A p-type silicon semiconductor film (thickness: 100 nm) was coated on the gray titanium oxide sintered material. For the product thus obtained, feeble magnetic wave radiation with respect to various organs and so forth was measured. Results of the measurement are shown in Table 1.

EXAMPLE 2

To a commercially available titanium oxide ($TiO_2$) powder (rutile type having an average particle diameter of 0.6 μm; manufactured by Furukawa Co., Ltd.), 3% of silicone varnish as a binder was added and mixed thoroughly. Thereafter, the mixture was press-molded in a mold under a pressure of about 600 kgf/cm$^2$ to obtain a molded material with a hemispherical columnar shape (in which the upper part was hemispherical and the lower part was a short circular column) as shown in part (b) of FIG. 1 (which is a perspective view showing the external appearance). More specifically, the molded material had a hemisphere with a diameter of 8 mm and a height of 1.5 mm formed on the upper surface of a circular column having a diameter of 8 mm and a height of 1.5 mm).

The molded material was sintered by heating at 1050° C. for 2 hours in a vacuum to obtain a black partially-reduced titanium oxide ($TiO_{1.86}$) sintered material.

On the black partially-reduced titanium oxide sintered material, a p-type germanium (containing aluminum at 100 at.ppm) semiconductor film was coated to a thickness of 100 nm by sputtering. For the product thus obtained, feeble magnetic wave radiation with respect to various organs and so forth was measured. Results of the measurement are shown in Table 2 below.

COMPARATIVE EXAMPLE 3

A sample was prepared in the same way as in Example 2 except that it was not coated with a p-type germanium semiconductor film. For the sample, which had only the black partially-reduced titanium oxide ($TiO_{1.86}$) sintered material as shown in part (b) of FIG. 1, feeble magnetic wave radiation with respect to various organs and so forth was measured. Results of the measurement are shown in Table 2.

TABLE 2

|  | Example 2 | Comparative Example 3 |
| --- | --- | --- |
| Titanium oxide base | $TiO_{1.86}$ | $TiO_{1.86}$ |
| p-type germanium thin film | present | not present |
| Immunity | +21 | +13 |
| Stomach | +19 | +10 |

TABLE 2-continued

|  | Example 2 | Comparative Example 3 |
| --- | --- | --- |
| Liver | +19 | +11 |
| Kidney | +18 | +10 |
| Blood circulation | +20 | +10 |
| Autonomous nervous system | +18 | +9 |
| Pain | +20 | +8 |

[Equipment used: MIRS]

EXAMPLE 3

To a commercially available titanium oxide ($TiO_2$) powder (rutile type having an average particle diameter of 0.6 μm; manufactured by Furukawa Co., Ltd.), 2% of silicone varnish as a binder was added and mixed thoroughly. Thereafter, the mixture was press-molded in a mold under a pressure of about 1,000 kgf/cm$^2$ to obtain a molded material with a conical columnar shape as shown in part (a) of FIG. 1, which was the same as in Example 1.

The molded material was sintered by heating at a temperature of from 900° C. to 1100° C. for 2 hours in a vacuum to obtain a black partially-reduced titanium oxide ($TiO_{1.85-1.95}$) sintered material.

The reason why there were variations in the reduced condition of the partially-reduced titanium oxide is that there were variations in the heating temperature, and that the samples were not simultaneously reduced in the same batch.

A p-type silicon semiconductor film (thickness: 100 nm±20 nm) was coated on the black partially-reduced titanium oxide sintered material. Samples thus prepared were affixed to meridian and affected parts (oppressive pain portions) with a commercially available adhesive tape in such a manner that the conical portions of the samples were pressed against the given parts.

Results of the treatment are shown in Table 3 below.

TABLE 3

|  | Age | Sex | Symptoms | Result of application |
| --- | --- | --- | --- | --- |
| 1 | 37 | female | heavy in leg, pain in temple | remarkably effective (A) |
| 2 | 27 | female | heavy in leg, stiff shoulder, sore heel | remarkably effective (A) |
| 3 | 19 | female | asthma, nasal congestion | remarkably effective (A) |
| 4 | 52 | male | lumbago | remarkably effective (A) |
| 5 | 40 | male | stiff shoulder | remarkably effective (A) |
| 6 | 21 | male | wisdom tooth ache and swelling | remarkably effective (A) |
| 7 | 40 | female | heavy in knee | remarkably effective (A) |
| 8 | 30 | male | stiff neck | effective (B) |
| 9 | 33 | female | morning sickness | remarkably effective (A) |
| 10 | 53 | male | stomachache | effective (B) |
| 11 | 22 | female | abdominal muscular pain | effective (B) |
| 12 | 57 | male | pain in leg | remarkably effective (A) |
| 13 | 10 | male | slight fever, inflammation of bladder | ineffective (D) |
| 14 | 20 | female | temporomandibular arthrosis | somewhat effective (C) |
| 15 | 19 | female | temporomandibular arthrosis | effective (B) |
| 16 | 29 | female | intercostal neuralgia | remarkably |

TABLE 3-continued

| Age | Sex | Symptoms | Result of application |
|---|---|---|---|
| 17 | 33 | female | temporomandibular arthrosis (recovered on third day) | effective (A) somewhat effective (C) |
| 18 | 31 | female | headache, temporomandibular arthrosis | remarkably effective (A) |
| 19 | 25 | male | lumbago | remarkably effective (A) |
| 20 | 30 | male | lumbago, constipation, stiff shoulder | effective (B) |
| 21 | 38 | male | stiffness in shoulder and neck | remarkably effective (A) |
| 22 | 55 | female | rheumatoid arthritis (swelling subsided) | somewhat effective (C) |
| 23 | 48 | male | cancer | ineffective (D) |
| 24 | 46 | male | sprain (under rehabilitation) | effective (B) |
| 25 | 38 | female | temporomandibular arthrosis | effective (B) |
| 26 | 50 | female | stiff shoulder, pain in right forefinger | somewhat effective (C) |
| 27 | 25 | female | temporomandibular arthrosis | effective (B) |
| 28 | 60 | female | stiff neck, so serious that neck could not be moved | remarkably effective (A) |
| 29 | 39 | female | stiff shoulder | remarkably effective (A) |
| 30 | 45 | female | temporomandibular arthrosis | remarkably effective (A) |
| 31 | 68 | male | lumbago | remarkably effective (A) |
| 32 | 47 | female | stiff shoulder | remarkably effective (A) |
| 33 | 52 | female | temporomandibular arthrosis, headache | effective (B) |
| 34 | 47 | male | high blood pressure, stiff shoulder | remarkably effective (A) |
| 35 | 23 | male | stiffness in neck and shoulder | remarkably effective (A) |
| 36 | 70 | male | swollen leg | remarkably effective (A) |
| 37 | 55 | female | lumbago, swollen leg | remarkably effective (A) |
| 38 | 70 | male | swelling | remarkably effective (A) |
| 39 | 40 | male | overweight (green tea treatment used jointly) 79 → 66 kg | somewhat effective (C) |
| 40 | 12 | female | constipation | remarkably effective (A) |

In this example (3), actual medical treatments were performed for patients of both sexes and various ages selected from the general public. Of forty patients, twenty-four patients showed remarkably favorable progress (A), nine patients showed favorable progress (B), five patients showed somewhat favorable progress (C), and two patients showed no change.

The total of the number of patients who showed remarkably favorable progress and the number of patients who showed favorable progress was 33. Hence, the percentage of effectiveness was 82.5%. Furthermore, weights were assigned to the results of the treatment as follows: 3 points to "remarkably effective"; 2 points to "effective"; 1 point to "somewhat effective"; and 0 point to "ineffective". The sum total of the points was divided by the total number of patients to calculate an effectiveness coefficient. In this example, it was 2.38, which was approximately the same as the results of disorder curing tests performed on Examples 1 and 2 (described later).

Thus, it has been recognized according to the studies conducted by the present inventors that the black partially-reduced titanium oxide sintered material according to the present invention is excellent in performance when the rate of reduction is between $TiO_2$ and $Ti_2O_3$. Therefore, in the case of $TiO_{2-x}$, $0<x<0.5$. In the case of $Ti_nO_{2n-1}$, $2.0<n<\alpha$.

In another experiment, test specimens were produced by sputtering a p-type amorphous silicon semiconductor on the respective surfaces of the black partially-reduced titanium oxide sintered material obtained in Example 1 and the white titanium oxide sintered materials obtained in Comparative Examples 1 and 2.

The test specimens were affixed to aching portions of patients' bodies. As a result, it was revealed that the black specimens had a greater curing effect.

However, if the sintered material as a base material is reduced to $Ti_2O_3$ ($TiO_{1.5}$), the curing effect lowers as shown by Comparative Example 2 in Table 1. Therefore, in the case of $TiO_{2-x}$, x is preferably within the range of $0<x<0.5$. It is most desirable that x be within the range of from 0.05 to 0.3.

In another experiment, a germanium semiconductor was deposited in place of the silicon semiconductor in Example 1 and Comparative Examples 1 and 2. In this case also, almost the same advantageous effects were obtained.

The film thickness is preferably within the range of from 1 nm to 500 nm. A film thickness of less than 1 nm could not give a satisfactory effect. When the film thickness exceeded 500 nm, only the effect of the semiconductor was available, and it became difficult for the partially-reduced titanium oxide to manifest its curing effect.

A more detailed examination revealed that a particularly desirable film thickness was from 50 nm to 200 nm, although it depended upon which part of the body the sample was affixed to.

Next, a test was performed on twenty-seven patients having stiffness in the shoulders.

Of fifteen patients using the samples of Example 1, twelve patients showed either remarkably favorable progress or favorable progress. The percentage of effectiveness was 80%.

Of twelve patients using the samples of Comparative Example 1, in which a p-type silicon semiconductor film was coated on titanium oxide ($TiO_2$), eight patients showed either remarkably favorable progress or favorable progress. The percentage of effectiveness was 67%.

Furthermore, weights were assigned to the results of the treatment as follows: 3 points to "remarkably effective"; 2 points to "effective"; 1 point to "somewhat effective"; and 0 point to "ineffective". The sum total of the points was divided by the total number of patients to calculate an effectiveness coefficient. The effectiveness coefficient of the samples of Example 1 was 2.20, and that of Comparative Example 1 was 1.83.

The results of the above-described test are shown in Table 4 below.

TABLE 4

| | Number of patients | Remarkably effective | Effective | Somewhat effective | Ineffective |
|---|---|---|---|---|---|
| Example 1 ($TiO_{1.91}$ × p-type Si) | 15 Ratio % Effectiveness % | 7 47 | 5 30 80 | 2 13 | 1 1 |
| | Number of patients | Remarkably effective | Effective | Somewhat effective | Ineffective |

TABLE 4-continued

| | | | | | | |
|---|---|---|---|---|---|---|
| Comparative Example 1 (TiO$_2$ × p-type Si) | 12 Ratio % Effectiveness% | 4 33 | 4 33 67 | 2 17 | 2 17 | |

In addition, a test was performed on twelve lumbago patients.

For six patients using the samples of Example 1, the percentage of effectiveness was 83%, whereas, for six patients using the samples of Comparative Example 1, the percentage of effectiveness was as low as 67%.

The effectiveness coefficient calculated as stated above by assigning 3 points to "remarkably effective", 2 points to "effective", 1 point to "somewhat effective", and 0 point to "ineffective" was 2.17 in the case of Example 1 and 1.83 in the case of Comparative Example 1.

The results of the above-described test are shown in Table 5 below.

TABLE 5

| | Number of patients | Remarkably effective | Effective | Somewhat effective | Ineffective |
|---|---|---|---|---|---|
| Example 1 (TiO$_{1.91}$ × p-type Si) | 6 Ratio % Effectiveness % | 3 50 | 2 33 83 | 0 0 | 1 17 |

| | Number of patients | Remarkably effective | Effective | Somewhat effective | Ineffective |
|---|---|---|---|---|---|
| Comparative (TiO$_2$ × p-type Si) | 6 Ratio % Effectiveness% | 2 33 | 2 33 67 | 1 17 | 1 17 |

The above-described examples revealed that the health support device according to the present invention is even more effective in curing physical disorders than the samples of the comparative example, in which titanium oxide (TiO$_2$) is coated with a silicon thin film, as in the conventional product.

As has been stated above, the health support device according to the present invention emits a great deal of feeble magnetic wave radiation and has far infrared radiation performance over a wide wavelength range. Therefore, the health support device is remarkably effective in curing disorders of various organs of the body.

What is claimed is:

1. A health support device comprising:

a partially-reduced sintered material of titanium oxide wherein a semiconductor film is laminated on the surface of a sintered material of low-order titanium oxide, represented by TiO$_{2-x}$, wherein 0<x<0.5.

2. The health support device according to claim 1, wherein said semiconductor film has a thickness of from 1 nanometer to 500 nanometers.

3. The health support device according to claim 1, wherein said semiconductor film is of one of silicon and germanium.

4. A health support device comprising:

a partially-reduced sintered material of titanium oxide, wherein a p-type semiconductor film is laminated on the surface of a sintered material of low-order titanium oxide represented by TiO$_{2-x}$, wherein 0<x<0.5.

5. The health support device according to claim 4, wherein said semiconductor film is of one of silicon and germanium.

6. The health support device according to claim 4, wherein said semiconductor film has a thickness of from 1 nanometer to 500 nanometers.

* * * * *